(12) United States Patent  
Durgin et al.

(10) Patent No.: US 8,832,160 B2  
(45) Date of Patent: Sep. 9, 2014

(54) METHODS AND SYSTEMS FOR CREATING AND UTILIZING A FIELD STRUCTURE

(75) Inventors: Matthew Barton Durgin, Scarborough, ME (US); Vladislav Vilensky, San Pedro, CA (US)

(73) Assignee: IDEXX Laboratories, Inc., Westbrook, ME (US)

(*) Notice: Subject to any disclaimer, the term of this patent is extended or adjusted under 35 U.S.C. 154(b) by 433 days.

(21) Appl. No.: 13/049,447

(22) Filed: Mar. 16, 2011

(65) Prior Publication Data

US 2012/0239426 A1 Sep. 20, 2012

(51) Int. Cl.  
*G06F 17/30* (2006.01)  
*G06F 19/00* (2011.01)

(52) U.S. Cl.  
CPC ........ *G06F 19/322* (2013.01); *G06F 17/30292* (2013.01)  
USPC .......................................................... 707/805

(58) Field of Classification Search  
CPC ................................................ G06F 17/30292  
USPC .......................................................... 707/805  
See application file for complete search history.

(56) References Cited

U.S. PATENT DOCUMENTS

| | | | |
|---|---|---|---|
| 2003/0158760 A1* | 8/2003 | Kannenberg | 705/4 |
| 2005/0015364 A1 | 1/2005 | Payton | |
| 2005/0257193 A1 | 11/2005 | Falk | |
| 2007/0162844 A1 | 7/2007 | Woodall | |
| 2008/0147436 A1* | 6/2008 | Ohlsson | 705/2 |
| 2008/0162428 A1 | 7/2008 | Gaurav | |
| 2010/0115446 A1 | 5/2010 | Fastabend | |
| 2010/0306195 A1 | 12/2010 | Wagener | |

* cited by examiner

*Primary Examiner* — William Spieler  
(74) *Attorney, Agent, or Firm* — McDonnell Boehnen Hulbert & Berghoff LLP

(57) ABSTRACT

A method and system for creating a name structure is provided. According to at least one embodiment, the method includes, for each data type of a plurality of data types, receiving an indication of a desired ordinal value of the data type and receiving an indication of a desired character length to associate with the data type. Based on the desired ordinal value and the desired character length of each data type of the plurality of data types, the method includes constructing a field structure that comprises a plurality of fields. Each field of the plurality of fields represents a unique data type of the plurality of data types and each field of the plurality of fields has a character length equal to the desired character length of the data type the given field represents. Additionally, each field of the plurality of fields is positioned in the field structure according to the desired ordinal value of the data type the given field represents.

17 Claims, 6 Drawing Sheets

FIG. 4

Name Structure — 402

| | Name Structure ^ | Active |
|---|---|---|
| ▶ | Production | Y |
| | Name Structure | N |
| | Name Structure | N |
| | Name Structure | N |

Add...
Print List...

Name Structure Details

Name: Production — 408

| Field Name ^ | Length ^ |
|---|---|
| A: Vet Code | 2 |
| E: Location | 3 |
| G: Animal Type | 1 |
| N: Sample Type | 1 |
| B: Owner Code | 3 |
| O: Reason | 2 |

— 406

Save
< Activate >
Print
Delete
Cancel

Structure: AAEEEGNBBBO — 412

Close

410

Data Types — 404

- A: Vet Code
- B: Owner Code
- C: Grower Code
- D: Complex
- E: Location
- F: Sub-Location
- G: Animal Type
- I: Breed 1
- J: Breed 2
- K: Year
- L: Placement
- M: Age
- N: Sample Type
- O: Reason

METHODS AND SYSTEMS FOR CREATING AND UTILIZING A FIELD STRUCTURE

BACKGROUND

Modern database and data warehousing systems are quite versatile. They can store vast amounts of data and recall such data quickly. Because of this, there is usually little hesitancy when storing data pertaining to a particular subject. Often, operators will store in a database as much data as is known about the particular subject. This data can be recalled later and used to generate various reports about the subject.

In the field of diagnostic testing, for example, a technician may prepare a batch of test subjects (sometimes referred to as "subjects-under-test") and send them to one or more diagnostic laboratories (labs). Each lab may perform different sets of diagnostics on the batch and may therefore require reports containing data specific to the set of diagnostics performed by that lab. For example, veterinary lab A may require data describing what animal type and breed each of the test subjects are, whereas veterinary lab B may require data describing what types of food each test subject ate.

Typically, no one lab is interested in all the possible data on a batch of test subjects. Rather, each lab may be interested in a different subset of the possible data. For each lab, technicians may design data reports to contain specific subsets of the possible subject-data based on the type of diagnostics performed by the lab. This process is often tedious and time consuming, especially when there are a large number of labs and/or a large number of test subjects. Therefore, it may be desirable to utilize a concise technique for defining the desired data to be used in a given data report. It may also be desirable to utilize a method for generating such data reports.

SUMMARY

In accordance with at least one embodiment described herein, a method of creating a field structure that represents a plurality of data types is disclosed. The method includes, for each data type of a plurality of data types, receiving an indication of a desired ordinal value of the data type and receiving an indication of a desired character length to associate with the data type. The indication of the desired ordinal value of the given data type is based on a drag and drop operation. The method further includes, based on the desired ordinal value and the desired character length of each data type of the plurality of data types, constructing a field structure that comprises a plurality of fields. Each field of the plurality of fields represents a unique data type of the plurality of data types and each field of the plurality of fields has a character length equal to the desired character length of the data type the given field represents. Additionally, each field of the plurality of fields is positioned in the field structure according to the desired ordinal value of the data type the given field represents.

In accordance with at least one embodiment described herein, a computing device is disclosed. Such a computing device includes a processor and data storage containing instructions executable by the processor for carrying out functions. The functions include, for each data type of a plurality of data types, receiving an indication of a desired ordinal value of the data type and receiving an indication of a desired character length to associate with the data type. The indication of the desired ordinal value of the given data type is based on a drag and drop operation. The functions further include, based on the desired ordinal value and the desired character length of each data type of the plurality of data types, constructing a field structure that comprises a plurality of fields. Each field of the plurality of fields represents a unique data type of the plurality of data types and each field of the plurality of fields has a character length equal to the desired character length of the data type the given field represents. Additionally, each field of the plurality of fields is positioned in the field structure according to the desired ordinal value of the data type the given field represents.

In accordance with at least one embodiment described herein, a non-transitory computer readable medium (CRM) is disclosed. The CRM contains instructions, which, when executed by a processor, cause the processor to carry out functions. The functions include for each data type of a plurality of data types, receiving an indication of a desired ordinal value of the data type and receiving an indication of a desired character length to associate with the data type. The indication of the desired ordinal value of the given data type is based on a drag and drop operation. The functions further include, based on the desired ordinal value and the desired character length of each data type of the plurality of data types, constructing a field structure that comprises a plurality of fields. Each field of the plurality of fields represents a unique data type of the plurality of data types and each field of the plurality of fields has a character length equal to the desired character length of the data type the given field represents. Additionally, each field of the plurality of fields is positioned in the field structure according to the desired ordinal value of the data type the given field represents.

These and other aspects will become apparent to those of ordinary skill in the art by reading the following detailed description, with reference where appropriate to the accompanying figures. Further, it should be understood that the embodiments noted herein are not intended to limit the scope of the invention as claimed.

BRIEF DESCRIPTION OF FIGURES

Various examples of the disclosed system and corresponding method are described herein with reference to the following figures, wherein like numerals denote like entities:

FIG. 4 is another example GUI, in accordance with an embodiment;

DETAILED DESCRIPTION

1. Introduction

As described above, in systems that use many different data types to describe subjects (e.g., test subjects), situations may call for generating a report (or some other deliverable) that describes each subject using a subset of the available data types. Depending on the situation, any particular subset of data types is said to describe or define the subjects. Different situations may call for describing or defining the subjects using different subsets of the available data types. Thus, the present application discloses, inter alia, methods and systems for defining a set of data types used to describe one or more subjects.

Accordingly, an example method of defining a set of data types used to describe a subject includes creating a field structure (sometimes referred to as a "name structure"). In at least one embodiment, a name structure takes the form of a string of characters, where each character refers to a specific data type. For example, one name structure may be six characters, three of which refer to a first data type, two of which refer to a second data type, and one of which refers to a third data type. The collective characters that refer to a specific data type may be referred to as data fields. Thus, this example data structure is said to have three data fields.

In at least one embodiment, a user may create different name structures in order to describe subjects in different ways (i.e., using different data types). For instance, as indicated above, a batch of subjects may undergo several different diagnostic tests at several different laboratories (labs). To facilitate the appropriate tests, each lab may desire that the subjects-under-test be described or defined with a specific subset of data types. This way, the labs may be able to tailor the tests according to the different kinds of subjects in the batch. Each lab may desire that subjects be defined with a subset of data different than other labs. Thus, for each different lab, a user can create a name structure unique to desires of that lab in order to describe or define the subjects-under-test.

A name structure may provide a definition of how subjects can be defined in one specific instance. In at least one embodiment, a user may create several instances of a particular name structure to define each subject of a batch. For example, a technician may create a separate instance of the name structure for each subject in a batch. In at least one embodiment, a user can populate the data fields of the instance with data codes. Each data code may be relatively short, and thus can be provided to a database as a key in order to retrieve longer descriptions (sometimes referred to as "data entries") of the subject. These longer descriptions may be presented to a user in the form of a print-out or displayed on a screen.

2. Example System Architecture

Figure 1:
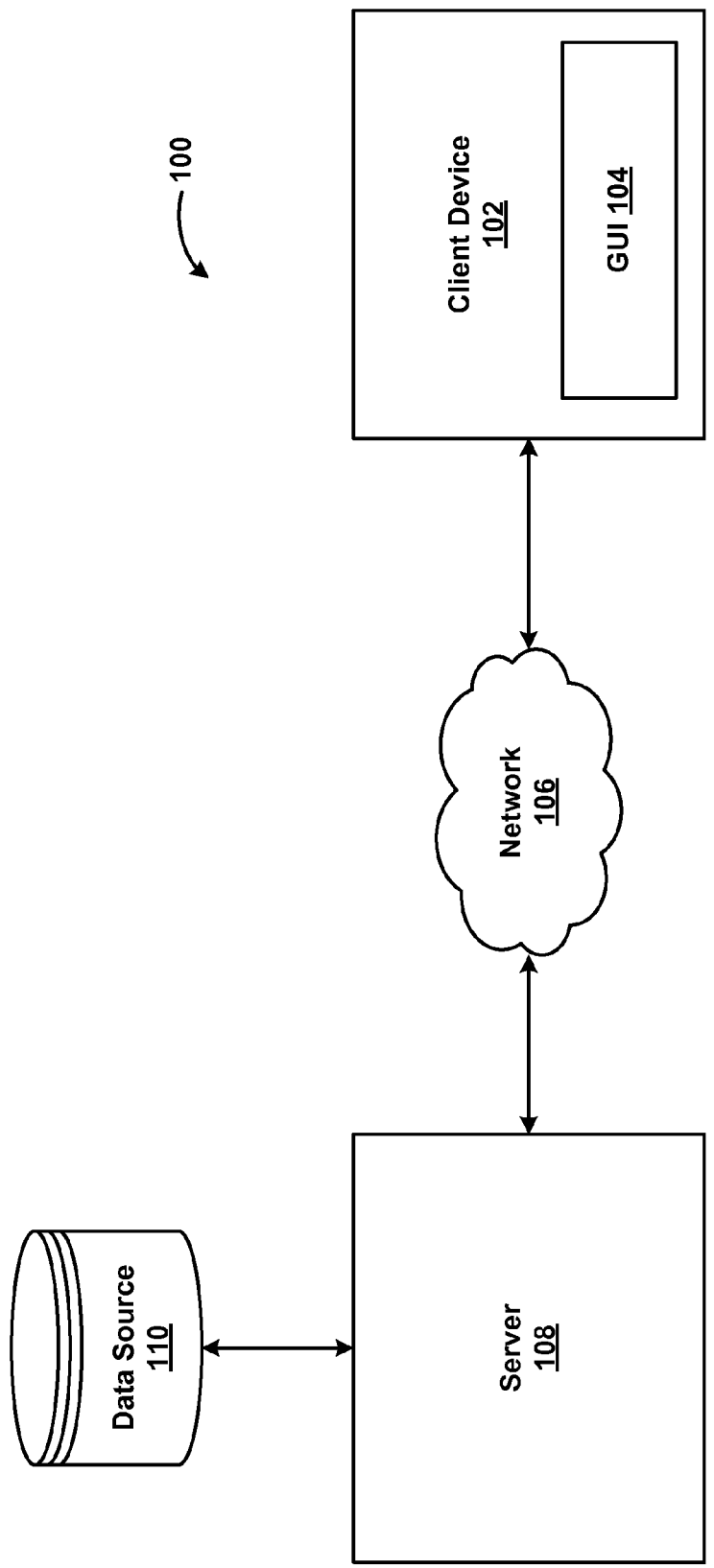
FIG. 1 is a block diagram illustrating an example system for creating a name structure, in accordance with an embodiment.

Referring now to FIG. 1, a high-level diagram is shown illustrating an example system 100 for creating and using a name structure. The example system 100 includes a client device 102 having incorporated therein a graphical user interface (GUI) 104, a network 106, a server 108, and a data source 110. Those skilled in the art will appreciate that system 100 is merely one example of a system that can be arranged to carry out at least one embodiment of the methods described herein. Certainly, other configurations of computing devices exist and can be arranged to carry out the disclosed methods.

In some arrangements, client device 102 may be a general purpose computing device (e.g., a personal computer) arranged to receive inputs from a user via GUI 104, and communicate with server 108 across network 106. Server 108 may be a general purpose server device arranged to host application programs and distribute data to various client devices. Network 106 may be a local area network, such as a corporate Ethernet, or a wide area network, such as the internet, for example. In general, client device 102 may be arranged to execute application programs resident at server 108 and present such programs at the client device 102 through a GUI 104. A user may manipulate the GUI 104 with various user-input devices to provide input instructions to the client device 102 and ultimately the server 108. Application programs executed on the client device 102 may be stored in memory storage of server 108 or in memory storage of client device 102, and provided using machine language instructions or software with object-oriented instructions, such as the Java programming language. However, other programming languages (e.g., C++) could be used as well.

In some arrangements, server 108 may be coupled to or integrated with a data source 110. Data source 110 may be any type of device such as a web server, application server, database or other data warehousing system, or any interface to another information provider. The data source 110 may provide to server 108 and client device 102 information content expressed in a markup language (e.g., Hypertext Markup Language (HTML), Extensible Markup Language (XML) with or without Extensible Style Sheets (XSL), VoiceXML, Extensible Hypertext Markup Language (XHTML), or Wireless Markup Language (WML)), for example.

Furthermore, data source 110 can be accessed through any type of network by the server 108 or client device 102. In some arrangements, server 108 acts as a proxy between the client device 102 and the data source 110. In some respects, the server 108 may operate as a client of the data source 110 to retrieve data content therefrom.

In some arrangements, server 108 and client device 102 reside on different platforms. For example, as shown in FIG. 1, server 108 may be hosted on a back-end server, and the client device 102 may be hosted on a PC or hand-held electronic device. However, in some different arrangements, server 108 and client device 102 reside on the same platform such as on an electronic device, if the platform or electronic device has the appropriate hardware and network capabilities. Thus, within some embodiments, functionality may be described as being part of the client device 102 or as being part of the server 108. Those skilled in the art will understand that the client device 102 the server 108 may co-exist on the same device, and thus functionality of either can be substituted by each other. Thus, the client device 102 may perform functions explained as being performed by the server 108, and the server 108 may perform functions explained as being performed by the client device 102. By utilizing the client/server arrangement, smaller electronic devices with limited hardware capability can access featured application programs and/or data.

Figure 2:
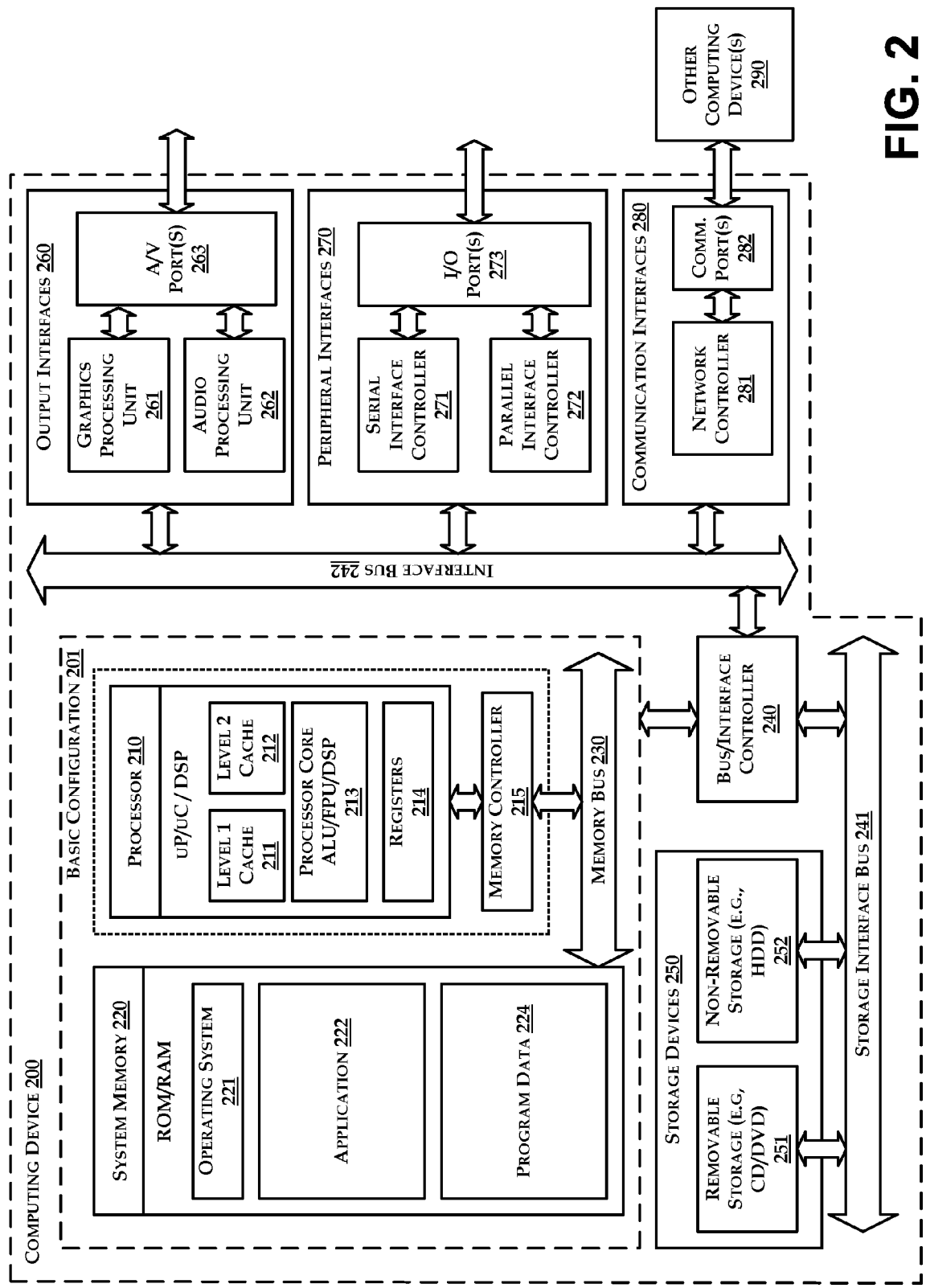
FIG. 2 is an example computing device, in accordance with an embodiment.

FIG. 2 is a block diagram illustrating an example computing device 200 that may be arranged to carry out at least one embodiment described herein. In other words, the computing device 200 may perform at least one method step of the present application, and/or the computing device 200 may include software designed to carry out at least one method step of the present application. Computing device 200 may be incorporated in or otherwise associated with client device 102, server 108, and/or data source 110 of system 100 in FIG. 1. For instance, at least part of client device 102 may encompass computing device 200.

In a basic configuration 201, computing device 200 includes one or more processors 210 and system memory 220. A memory bus 230 can be used for communicating between the processor 210 and the system memory 220.

Depending on the desired configuration, processor 210 can be of any type including but not limited to a microprocessor (µP), a microcontroller (µC), a digital signal processor (DSP), or any combination thereof. Processor 210 can include one more levels of caching, such as a level one cache 211 and a level two cache 212, a processor core 213, and registers 214. The processor core 213 can include an arithmetic logic unit (ALU), a floating point unit (FPU), a digital signal processing core (DSP Core), or any combination thereof. A memory controller 215 can also be used with the processor 210, or in some implementations the memory controller 215 can be an internal part of the processor 210.

Depending on the desired configuration, the system memory 220 can be of any non-transitory type memory including but not limited to volatile memory (such as RAM), non-volatile memory (such as ROM, flash memory, etc.) or any combination thereof. System memory 220 includes an operating system 221, one or more applications 222, and program data 224. For example, an application 222 may be designed to present a GUI to receive certain inputs from a user. Based on those inputs, application 222 may create a name structure, reference data source 110, present data to the user, or take any other action in accordance with at least one embodiment described herein as well as provide various electrical signals to various other components of computing device 200.

Computing device 200 can have additional features or functionality, and additional interfaces to facilitate communications between the basic configuration 201. For example, a bus/interface controller 240 can be used to facilitate communications between the basic configuration 201 and one or more data storage devices 250 via a storage interface bus 241. The data storage devices 250 can be removable storage devices 251, non-removable storage devices 252, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media can include volatile and nonvolatile, removable and non-removable media implemented in any method or technology for storage of information, such as computer readable instructions, data structures, program modules, or other data.

System memory 220, removable storage 251 and non-removable storage 252 are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 200. Any such computer storage media can be part of device 200.

Computing device 200 can also include an interface bus 242 for facilitating communication from various interface devices to the basic configuration 201 via the bus/interface controller 240. Example output interfaces 260 include a graphics processing unit 261 and an audio processing unit 262, which can be configured to communicate to various external devices such as a display screen associated with client device 102, or speakers via one or more A/V ports 263. Example peripheral interfaces 260 include a serial interface controller 271 or a parallel interface controller 272, which can be configured to communicate with external devices such as user-input devices (e.g., keyboard, mouse, pen, voice input device, touch input device, etc.) or other peripheral devices (e.g., printer, scanner, etc.) via one or more I/O ports 273. An example communication interface 280 includes a network controller 281, which can be arranged to facilitate communications with one or more other computing devices 290 (e.g., server 108) over a network communication via one or more communication ports 282. The communication connection is one example of a communication media. Communication media may typically be embodied by computer readable instructions, data structures, program modules, or other data in a modulated data signal, such as a carrier wave or other transport mechanism, and includes any information delivery media. A "modulated data signal" can be a signal that has one or more of its characteristics set or changed in such a manner as to encode information in the signal. By way of example, and not limitation, communication media can include wired media such as a wired network or direct-wired connection, and wireless media such as acoustic, radio frequency (RF), infrared (IR) and other wireless media.

As described above, computing device 200 can be incorporated in at least one of client device 102, server 108, or data source 110, implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 200 can also be implemented as a personal computer including both laptop computer and non-laptop computer configurations.

3. Manual Name Structure Creation

Figure 3:
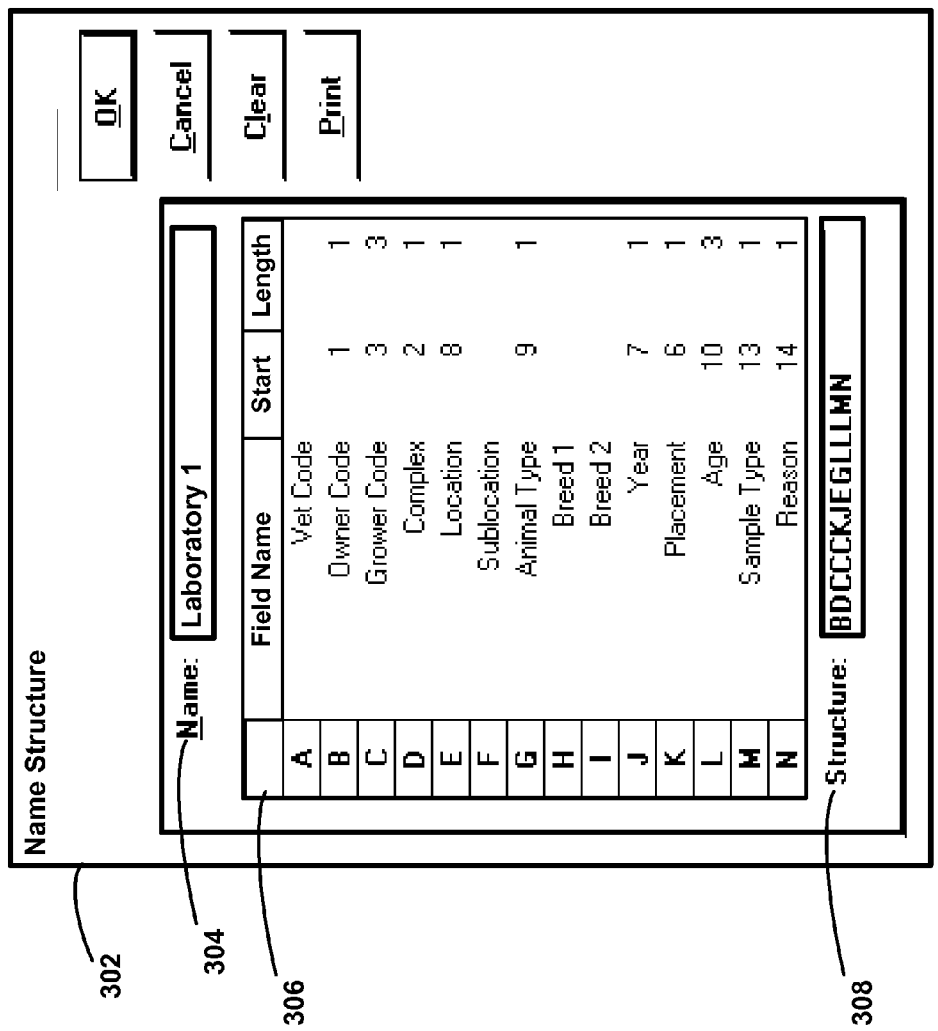
FIG. 3 is an example GUI, in accordance with an embodiment.

FIG. 3 is an illustration of example GUI 302 used to facilitate the creation of a name structure. In some embodiments, GUI 302 is presented to a user on a display device at client device 102. The user may interact with GUI 302 by manipulating one or more user-input devices (e.g., a keyboard and/or mouse) to provide operating instructions to the GUI 302 and ultimately to the client device 102, server 108, and data source 110.

GUI 302 includes a data box 306 that contains rows labeled "A" through "N" (more or fewer rows may be included). Each row lists a different field name. For example, row "A" lists field name "Vet Code;" row "B," "Owner Code;" row "C," "Grower Code," and so on through row "N," "Reason." For brevity's sake, each row is referred to as its own "data type." Thus, data relating to "Vet Code" is said to be of "data type A," whereas data relating to "Animal Type" is said to be of "data type G." GUI 302 may include other ancillary features, such as a box 304 for naming the current name structure, and various command buttons for saving the input, deleting or cancelling the input, clearing the current entry, and printing the screen.

A particular subject (e.g., test subject), and perhaps, each of a batch of subjects, may have data stored that describes the test subject according to each of the listed field names. For example, a first test subject may have data entries relating to a vet code, an owner code and animal type (as well as the rest of the data types) stored in data source 110. A second test subject may also have data entries relating to a vet code, owner code, and animal type (as well as the rest of the data types) stored in data source 110, and each may be the same or different than the first test subject's respective vet code, owner code, and animal type. This data may be stored in data source 110 arranged in tables according to subject or data type. Those skilled in the art will realize that GUI 302 lists 14 data types, each having general veterinary context. However, these data types are merely examples, and data types having any context are certainly possible, as are more or fewer data types. Further, data stored in data source 110 that describes one or more subjects according to one or more data types may be arranged in any manner, the details of which are not relevant to the present application.

In at least one embodiment, a user can utilize GUI 302 to choose from among the available data types to create a specific name structure. In the context of GUI 302, a user can create a name structure by defining at which character position of the name structure each desired data type starts and the corresponding character length of the data type. To do so, the user may position a screen cursor (e.g., by use of a mouse) in the "start" box adjacent to the desired data type and enter (e.g., by use of a keyboard) the starting character for that data type. The user may then position the cursor in the "Length" box adjacent to the start box and enter a desired character length for that data type.

For example, a user may position the cursor in the start box adjacent to Owner Code and enter a "1" to signify that the first character of the name structure is of type Owner Code (i.e., data type B). The user may then position the cursor in the length box adjacent to the start box and enter a "1" to signify that the owner code data type occupies (1) one character in the name structure.

If the user desires the "Complex" data type to be the next identified data type in the name structure, the user would position the cursor in the start box adjacent to Complex and enter the appropriate character position at which the Complex data type should start. In the current example, the Complex data type should start at character position (2) two because the first data type (i.e., Owner Code) started at character position 1 and has a length of 1. The user may then position the cursor in the length box adjacent to the start box and enter the desired length for given data type, which in this example is "1."

If the user desires the "Grower Code" data type to be the next identified data type in the name structure, the user would position the cursor in the start box adjacent to Grower Code and enter the appropriate character position at which the Grower Code data type should start. In the current example, the Grower Code data type should start at character position (3) three because the first data type (i.e., Owner Code) started at character position 1 and has a length of 1, and the second data type started at character position 2 and has a length of 1. The user may then position the cursor in the length box adjacent to the start box and enter the desired length for the given data type, which in this example is "3."

The user may continue in this manner, identifying the character start position and character length for each data type desired for the given name structure. The software module may construct the name structure based on the user's inputs in the various start and length boxes. The name structure of the present example is shown in box 308 and takes the form "BDCCCKJEGLLLMN." Thus, subjects that are to be described according to this name structure will be described with 14 characters, where the first character is of data type B, the second character is of data type D, the third, fourth, and fifth characters are of data type C, the sixth character is of data type K, the seventh character is of data type J, the eighth character is of data type E, the ninth character is of data type G, the tenth, eleventh, and twelfth characters are of data type L, the thirteenth character is of data type M, and the fourteenth character is of data type N.

As described, the user may manually enter the starting character and length of each desired data type in the data structure. The starting character of a given data type depends on the number of data types preceding the given data type in the name structure and their character lengths. If a user enters an erroneous character start position for some data type (e.g., the previous data types and their lengths dictate that the next character start position is "12," but the user enters something other than "12"), the software module may overwrite the portion of the name structure that overlaps with the desired character start position, produce an error, or take some other undesirable result. Thus, when utilizing the manual name structure creation method, a user may take extra care in entering the character start positions or encounter at least one error of some kind.

4. Automatic Name Structure Creation

FIG. 4 is an illustration of another example GUI 402 used to facilitate another name structure creation method, namely an automatic name structure method. In some embodiments, GUI 402 is presented to a user on a display device at client device 102. The user may interact with GUI 402 by manipulating one or more user-input devices (e.g., a keyboard and/or mouse) to provide operating instructions to the GUI 402 and ultimately to the client device 102, server 108, and data source 110.

Shown adjacent to GUI 402 is a "Data Types" window 404. The window 404 may be included within the GUI 402, or provided as a separate GUI. Window 404 lists 14 example visual representations of available data types. GUI 402 includes a name structure details box that includes an area 406 for collecting the data types desired to form the name structure, and a box 408 for naming the particular name structure. In some embodiments, GUI 402 also includes various other ancillary features, such as a box 410 for switching to a previously defined name structure, and command buttons for adding a new name structure, saving the input, deleting or cancelling the input, clearing the current entry, and printing the screen.

In at least one embodiment, a user may utilize GUI 402 to create a name structure by manipulating GUI 402 so as to drag and drop visual indications of the desired data types from window 404 to box 406. The user may also enter a desired character length in a "Length" box adjacent to each desired data type. Based on the order in which a user drags and drops visual indications of the desired data types, and based on the desired length of each data type entered by the user (or determined in some other manner), the software module automatically determines the name structure.

In the context of GUI 402, for example, a user may position a screen cursor (e.g., by use of a mouse) over a visual indication of the first desired data type (e.g., data type A (Vet Code)) and engage the cursor (e.g., by clicking the mouse). The user may then reposition the cursor to somewhere within box 406 and disengage the cursor. The software module may associate this interaction with defining data type A as the first data type in the data structure. The software module may locate the visual indication (or a copy thereof) to the top of box 406. Those skilled in the art will realize that this is merely an example of a drag-and-drop operation. Certainly, other ways of effecting a drag-and-drop operation are possible as well and may be used in the present context (e.g., engaging the cursor by clicking and releasing the mouse button a first time and disengaging the cursor by clicking and releasing the mouse button a second time).

If the user desires another data type to be present in the current name structure, the user may position the cursor over a visual indication of the next desired data type (e.g., data type E (Location)) and drag and drop the visual indication from window 404 to box 406. The user may repeat this process until visual indications of each desired data type appear in box 406 (e.g., data type A (Vet Code), data type E (Location), data type G (Animal Type), data type N (Sample Type), data type B (Owner Code), and data type O (Reason)). Based on the order in which the user dragged-and-dropped each of the desired data types, the software module positions the data fields in the name structure accordingly. Thus, the first data type dragged-and-dropped will be the first data field in the name structure. The second data type dragged-and-dropped will be the second data field in the name structure, and so on.

At any point in the process, a user may enter (e.g., by use of a keyboard) the desired character length of each of the data types. To do so, the user may position the cursor in the length box adjacent to a particular data type and enter the desired length. In the context of example GUI 402, data type A has length "2," data type E has length "3," data type G has length "1," data type N has length "1," data type B has length "3," and data type O has length "2." In at least one embodiment, the character lengths for each data type are previously defined (e.g., by a user or otherwise) and the character length box is automatically populated with the appropriate character length upon a drag-and-drop operation.

Based on the order in which the user dragged-and-dropped each of the desired data types, and based on the character lengths of each data type, the software module may automatically generate the name structure. The software module may determine the starting character position of each given data field based on the character lengths data fields having a higher ordinal priority than the given data field. The software module may add the character lengths of the data types having higher ordinal priority and add 1 to that number to determine the starting character position of a given data type. For data type G, for instance, data type A, and E have higher ordinal priorities and their summed character length is 5. Adding 1 to this number, the software module determines that the starting character position in the name structure for data type G is 6.

In the context of example GUI 402, the complete name structure is shown in box 412 and takes the form "AAEEE-GNBBBO." Thus, subjects that are to be described according to this name structure will be described with 11 characters, where the first and second character is of data type A, the third, fourth and fifth characters are of data type E, the sixth character is of data type G, the seventh character is of data type N, the eighth, ninth, and tenth characters are of data type B, and the eleventh character is of data type O.

Figure 5:
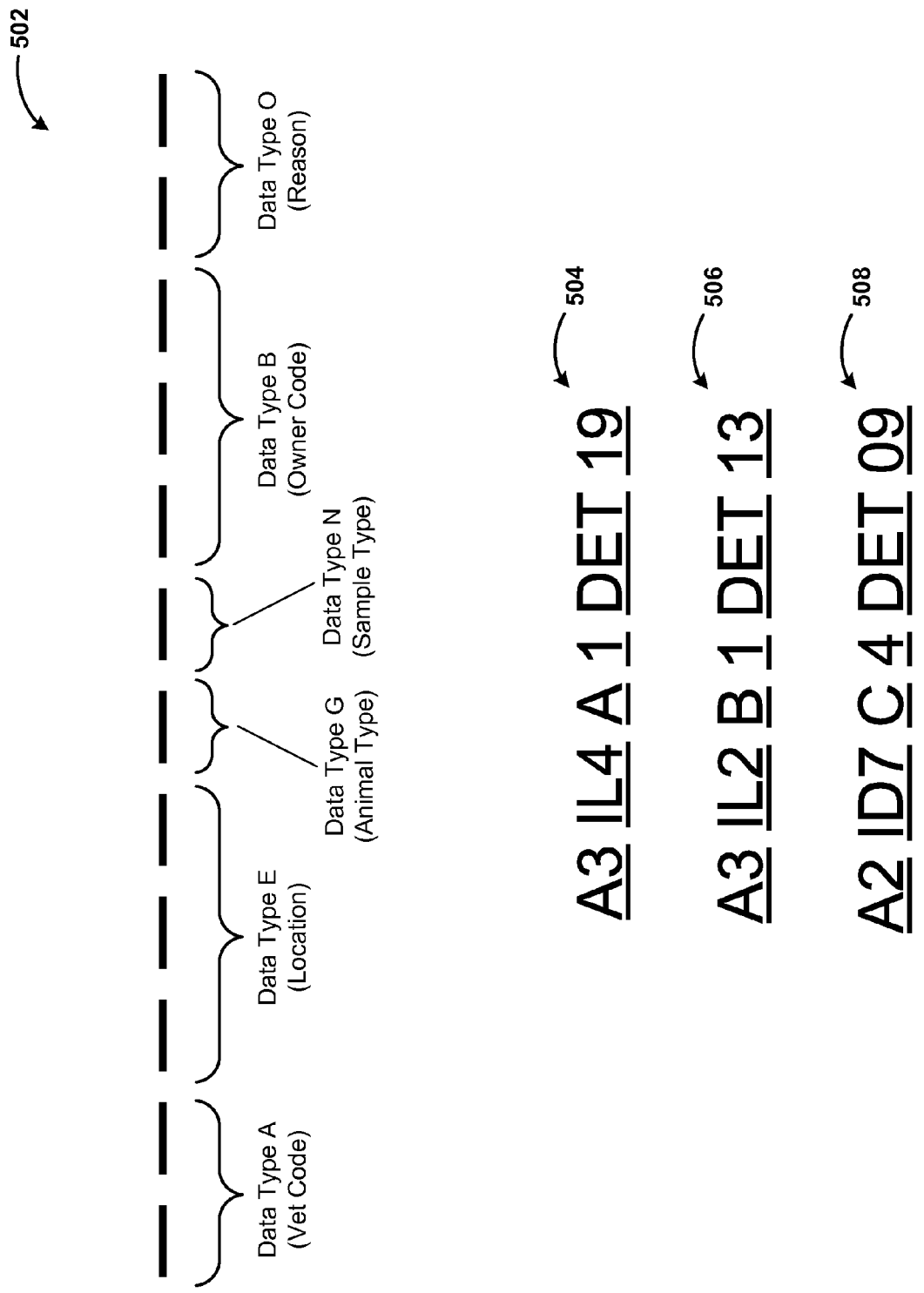
FIG. 5 illustrates an example name structure and example instances of the name structure, in accordance with an embodiment.

FIG. 5 illustrates a name structure 502 created with example GUI 402 and several instances 504, 506, 508 of the name structure 502. In one example, a name structure (e.g., name structure 502) provides a definition of how to describe a particular subject (e.g., a test subject) and to what type of data each character in the string of characters refers. Thus, for any given name structure, a subject can be described with a character string and each character (or group of characters) in the string refers to a particular data type. Subjects can be described according to any number of different name structures, depending usually on the application.

Name structure 502 is shown having six different data fields: data type A (two characters long), data type E (3 characters long), data type G (one character long), data type N (one character long), data type B (three characters long), and data type O (one character long).

Upon creating a name structure, a user may create several instances of that name structure, one for each subject. The user may populate the data fields of a particular instance with data codes that refer to the appropriate data type. For example, in instance 504, the first data field (Vet Code) may be populated with the data code "A3." A3 may refer to some type of Veterinarian, the details of which may be defined in data source 110. The second data field (Location) may be populated with the data code "IL4." IL4 may refer to some location, the details of which may be also be defined in data source 110. The remaining data fields of example instance 504 are populated with data codes "A," "1," "DET," and "19," respectively. Each data code may be further defined in data source 110.

Additional example name structure instances 506 and 508 are shown to contrast example name structure instance 504. Instance 506 is populated with data codes "A3IL2B1DET13" and instance 508 is populated with data codes "A2ID7C4DET09." Instance 506, for example, has several data fields populated with the same data codes as instance 504, namely data type A, data type N, and data type B. Instance 506 has several data fields populated with different data codes than instance 504, namely, data type E, data type G, and data type O. Thus, subjects of a batch of test subjects, for example, may be uniquely indentified based on their data fields.

A user may create instances of name structures by way of any of the previously discussed GUIs or perhaps an additional GUI (not shown). Those skilled in the art will realize that these are merely example instances of an example name structure populated with example data codes. Other data codes and other name structures are possible as well.

The name structure and instances of the name structure allow a user to specify for each subject several pieces of information in a shortened notation. In at least one embodiment, a user may populate an instance of name structure 502 with the data fields of example instance 506, namely "A3IL4A1DET19." A user may wish to generate a report (or some other deliverable) in which further definitions of the data codes are presented. It at least one embodiment, a software module may split the instance into respective data codes and use each data code as a key to retrieve from data source 110 data entries corresponding to the respective data codes.

For example, the software module may present "A3" to data source 110 as a key. The data code "A3" is populated in the data type A data field. Thus, the software module may look to a database table in data source 110 relating to Data Type A (Vet Code) and run a search operation for "A3." For instance, data code "A3" may refer to a data entry "Matt Armstrong's Veterinary Services, Inc." The software module may retrieve this data entry and present it in a report of some kind, display it on a screen, or present it in some other manner.

The software module may next refer to data code "IL4" and use it as a key in data source 110. The software module may look to a database table in data source 110 relating to data type E and run a search operation for "IL4." For instance, "IL4" may refer to a data entry "Cook County, Illinois, USA." The software module may retrieve this data entry and present it in some manner. The software may repeat this procedure for each data code in a name structure instance, and perhaps for each data code in each name structure instance of a batch of name structure instances. Those skilled in the art will realize that the same software module or system used to create the name structure may carry out the data code lookup procedure. In some embodiments, a different software module or system may carry out the data code lookup procedure. Additionally, data codes may be used for any other conceivable purpose as well.

5. Example Operation

Figure 6:
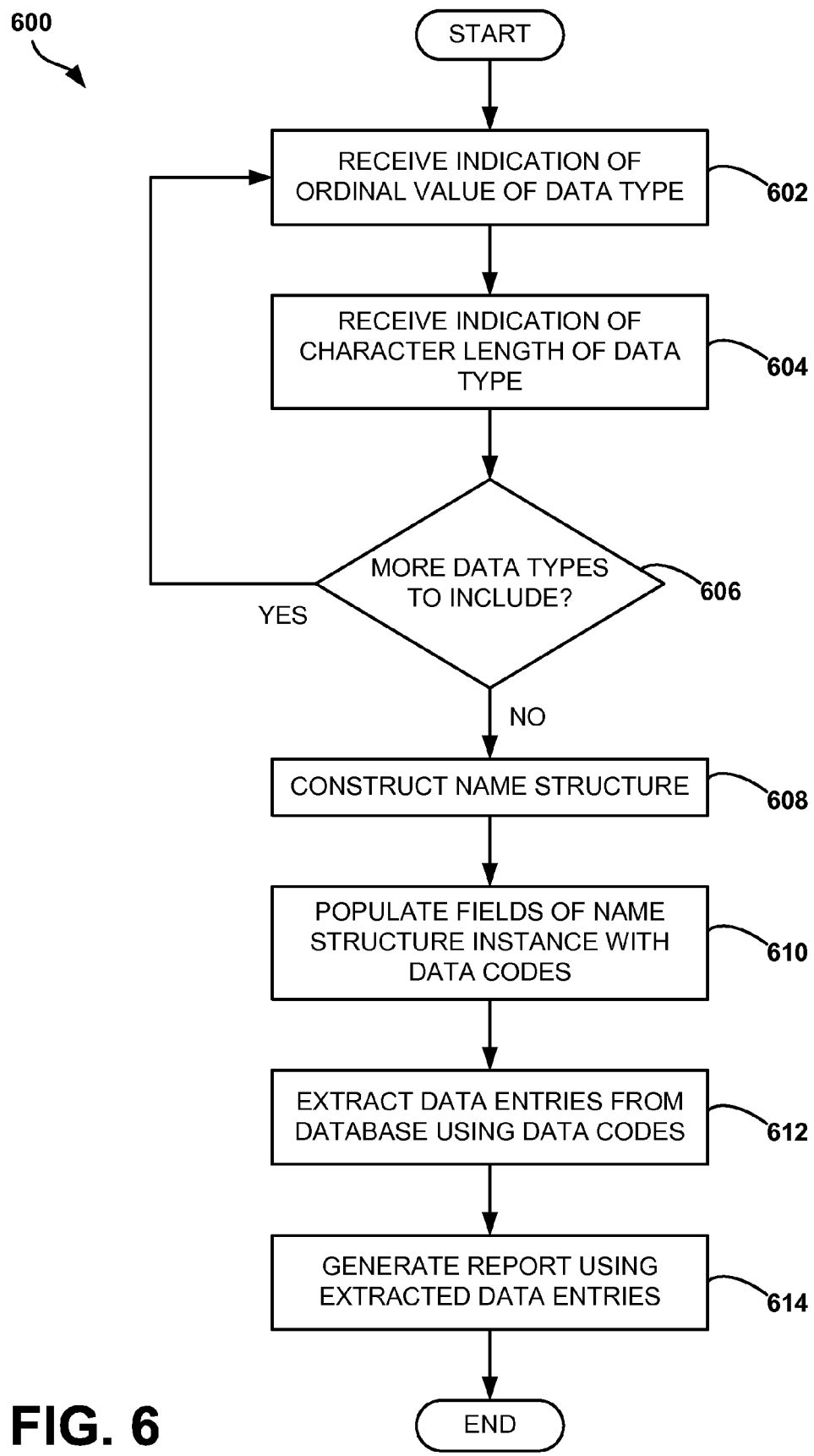
FIG. 6 is a flow diagram illustrating an example method, in accordance with an embodiment.

FIG. 6 is a flow diagram illustrating an example name structure creation process according to at least one embodiment described herein. The example process may include one or more operations, functions, or actions as illustrated by one or more of blocks 602, 604, 606, 608, 610, 612, and/or 614. Those skilled in the art will understand that the flow diagram of FIG. 6 illustrates functionality and operation of one possible implementation of the present embodiments described herein. In this regard, each block of each flow diagram may represent a module, a segment, or a portion of program code, which includes one or more instructions executable by a processor for implementing specific logical functions or steps in the process. The program code may be stored on any type of computer readable medium (e.g., computer readable storage medium or non-transitory media), for example, such as a storage device including a disk or hard drive. In addition, each block may represent circuitry that is wired to perform the specific logical functions in the process. Alternative implementations are included within the scope of the example embodiments of the present application in which functions may be executed out of order from that shown or discussed, including substantially concurrent or in reverse order, depending on the functionality involved, as would be understood by those reasonably skilled in the art.

Flow begins at block 602 where the system receives an indication of the ordinal value of a data type. In at least one embodiment, the system may receive the indication from a user based on a drag-and-drop operation, as described above. Thus, the system may associate an ordinal priority with a given data type based on the order in which the given data type was dragged-and-dropped from a first GUI window location to a second GUI window location. For example, the system may associate the highest (or first) ordinal priority to the first data type dragged-and-dropped. Alternatively, the system may associate the highest ordinal priority to the data type dragged-and-dropped to a specific GUI window position (e.g., the top of the list). The system may determine ordinal priorities for data types in other suitable manners as well.

At block 604, the system receives an indication of a character length of the data type. In at least one embodiment, a user positions a screen cursor in a box adjacent to the data type and enters (e.g., by using a keyboard) a number of desired characters. In at least one embodiment, the number of characters for each data type is predetermined.

At block 606, if there are more data types to include in the name structure, flow may return to block 602 and a user may, for example, drag-and-drop a visual indication of another data type. In at least one embodiment, if there are no more data types to include, a user may press a button or make some other indication, (e.g., do nothing) to the system to construct the name structure at block 608. The system may construct the name structure according to the procedure described above. Thus, the system may allocate a number of characters for the name structure in accordance with the sum of all the desired data types' character lengths. For each specific desired data type, the system may determine as the starting character position in the name structure the sum of character lengths of data types having a higher ordinal priority than the given data type plus one.

At block 610, the system (or a user) may optionally create an instance of the created name structure to describe a particular subject (e.g., a test subject). In at least one embodiment, a user populates the data fields of the name structure with data codes, as described above. A user may do so by way of a GUI, for example.

At block 612, the system may extract a data entry from a database using at least one data code populated in a particular instance as a key, as described above. In at least one embodiment, the system may refer to a specific table in a database and run a search operation using a data code populated in an instance. In at least one embodiment, the data code is a shortened version of a specific data entry.

And at block 614, the system may collect the extracted data entries and present them in a report print-out, display them on a screen, or present them in some other manner. The system may collect each data entry and group them according to subject. In at least one embodiment, the system may collect data entries for each of a batch of subjects and present the data entries in a consolidated report. Certainly, other ways of presenting data entries exist as well and may be used.

6. Conclusion

It should be understood that the programs, processes, methods and systems described herein are not related or limited to any particular type of computer or network system (hardware or software), unless indicated otherwise. Various types of general purpose or specialized computer systems may be used with or perform operations in accordance with the teachings described herein.

It should be further understood that these and other arrangements described herein are for purposes of example only. As such, those skilled in the art will appreciate that other arrangements and other elements (e.g. machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location.

In view of the wide variety of embodiments to which the principles of the present application can be applied, it should be understood that the illustrated embodiments are exemplary only, and should not be taken as limiting the scope of the present application. For example, the steps of the flow diagrams may be taken in sequences other than those described, and more or fewer elements may be used in the block diagrams. While various elements of embodiments have been described as being implemented in software, in other embodiments in hardware or firmware implementations may alternatively be used, and vice-versa.

Note that while the present application has been described in the context of a fully functional server and client device system and method, those skilled in the art will appreciate that mechanisms of the present application are capable of being distributed in the form of a non-transitory computer-readable medium of instructions in a variety of forms, and that the present application applies equally regardless of the particular type of signal bearing media used to actually carry out the distribution. For example, a computer usable medium can include a readable memory device, such as a hard drive device, CD-ROM, a DVD-ROM, or a computer diskette, having computer readable program code segments stored thereon. The computer readable medium can also include a communications or transmission medium, such as, a bus or a communication link, either optical, wired or wireless having program code segments carried thereon as digital or analog data signals. As such, the methods described herein may be embodied in a computer program product that includes one or more computer readable media, as described as being present within the server 108 or the client device 102.

The claims should not be read as limited to the described order or elements unless stated to that effect. Therefore, all embodiments that come within the scope of the following claims and equivalents thereto are claimed as the invention.

What is claimed is:
1. In a computing device, a method of creating a field structure that represents a plurality of data types, the method comprising:
for each given data type of the plurality of data types, the computing device receiving from a user an indication of a desired ordinal value of the given data type, the indi- cation of the desired ordinal value of the given data type being based on a drag and drop operation performed by the user;

for each given data type of the plurality of data types, the computing device receiving from the user an indication of a desired character length to associate with the given data type;

based on (i) the desired ordinal value and (ii) the desired character length of each data type of the plurality of data types, the computing device constructing a string structure that comprises a plurality of fields,
- wherein each field of the plurality of fields comprises a number of instances of a given character representing a unique data type of the plurality of data types, the number of instances of a given character in a given field being equal to the desired character length of the data type the given field represents, and
- wherein each field of the plurality of fields is positioned in the field structure according to the desired ordinal value of the data type the given field represents;

the computing device constructing a string based on the string structure by assembling a plurality of data codes based on an input from the user, each respective data code of the plurality of data codes representing a unique data type of the plurality of data types;

for each respective data code assembled in the string, the computing device using the respective data code as a key to extract a respective data-entry from an associated database; and the computing device generating a report using each extracted data-entry.

2. The method of claim 1, wherein the desired ordinal value of the data type is commensurate with an order in which the user drags a visual representation of the data type from a first graphical user interface (GUI) location and drops the visual representation in a second GUI location.

3. The method of claim 2, wherein the order in which the user drags a visual representation of the data type from a first GUI location and drops the visual representation in a second GUI location is established by the user manipulating a user-input device coupled to the computing device.

4. The method of claim 1, wherein the indication of a desired character length to associate with the given data type is established by the user manipulating a user-input device coupled to the computing device.

5. The method of claim 1, wherein based on (i) the desired ordinal value and (ii) the desired character length of each data type of the plurality of data types, the computing device constructing a string structure that comprises a plurality of fields comprises:
- for each given field of the plurality of fields, the computing device summing character lengths of all data types with higher ordinal priorities than the data type that the given field represents; and
- for each given field of the plurality of fields, the computing device determining as a starting character position within the string structure for the given field a character position equal to the summed character lengths plus one.

6. The method of claim 1, further comprising:
the computing device constructing several strings based on the string structure by assembling additional data codes such that each string contains a unique combination of data codes, each string thereby identifying a unique subject.

7. The method of claim 6, wherein the subjects identified by the strings field structure instances are veterinary diagnostic subjects.

8. A computing device comprising:
a processor; and
data storage containing instructions executable by the processor for carrying out functions, the functions comprising:

for each given data type of a plurality of data types, receiving from a user an indication of a desired ordinal value of the given data type, the indication of the desired ordinal value of the given data type being based on a drag and drop operation performed by the user;

for each given data type of the plurality of data types, receiving from the user an indication of a desired character length to associate with the given data type;

based on (i) the desired ordinal value and (ii) the desired character length of each data type of the plurality of data types, constructing a string structure that comprises a plurality of fields,
- wherein each field of the plurality of fields comprises a number of instances of a given character representing a unique data type of the plurality of data types, the number of instances of a given character in a given field being equal to the desired character length of the data type the given field represents, and
- wherein each field of the plurality of fields is positioned in the field structure according to the desired ordinal value of the data type the given field represents;

constructing a string based on the string structure by assembling a plurality of data codes based on an input from the user, each respective data code of the plurality of data codes representing a unique data type of the plurality of data types;

for each respective data code assembled in the string, using the respective data code as a key to extract a respective data-entry from an associated database; and generating a report using each extracted data-entry.

9. The computing device of claim 8, further comprising a graphical user interface (GUI) coupled to or integrated in the processor, wherein the desired ordinal value of the data type is commensurate with an order in which the user drags a visual representation of the data type from a first GUI location and drops the visual representation in a second GUI location.

10. The computing device of claim 9, further comprising a user-input device coupled to the processor, wherein the order in which the user drags a visual representation of the data type from a first GUI location and drops the visual representation in a second GUI location is established by the user manipulating the user-input device.

11. The computing device of claim 8, further comprising a user-input device coupled to the processor, wherein the indication of a desired character length to associate with the given data type is established by the user manipulating the user-input device.

12. The computing device of claim 8, wherein based on (i) the desired ordinal value and (ii) the desired character length of each data type of the plurality of data types, constructing a string structure that comprises a plurality of fields comprises:
- for each given field of the plurality of fields, summing character lengths of all data types with higher ordinal priorities than the data type that the given field represents; and
- for each given field of the plurality of fields, determining as a starting character position within the string structure for the given field a character position equal to the summed character lengths plus one.

13. The computing device of claim 8, wherein the functions further comprise:

constructing several strings based on the string structure by assembling additional data codes such that each string contains a unique combination of data codes, each string thereby identifying a unique subject.

14. The computing device of claim 13, wherein the subjects identified by the strings are veterinary diagnostic subjects.

15. A non-transitory computer readable medium (CRM) having software instructions stored thereon, which, when executed by a computing device, cause the computing device to carry out functions, the functions comprising:

for each given data type of a plurality of data types, receiving from a user an indication of a desired ordinal value of the given data type, the indication of the desired ordinal value of the given data type being based on a drag and drop operation performed by the user;

for each given data type of the plurality of data types, receiving from the user an indication of a desired character length to associate with the given data type;

based on (i) the desired ordinal value and (ii) the desired character length of each data type of the plurality of data types, constructing a string structure that comprises a plurality of fields, wherein each field of the plurality of fields comprises a number of instances of a given character representing a unique data type of the plurality of data types, the number of instances of a given character in a given field being equal to the desired character length of the data type the given field represents, and wherein each field of the plurality of fields is positioned in the field structure according to the desired ordinal value of the data type the given field represents;

constructing a string based on the string structure by assembling a plurality of data codes based on an input from the user, each respective data code of the plurality of data codes representing a unique veterinary diagnostic subject;

for each unique veterinary diagnostic subject identified by a given string, using the respective data codes of the given string as keys to extract respective data-entries from an associated database; and generating a report for the veterinary diagnostic subject using each extracted respective data-entry.

16. The CRM of claim 15, wherein the desired ordinal value of the data type is commensurate with the order in which the user manipulates a user-input device to drag a visual representation of the data type from a first graphical user interface (GUI) location and drop the visual representation in a second GUI location.

17. The CRM of claim 15, wherein based on (i) the desired ordinal value and (ii) the desired character length of each data type of the plurality of data types, constructing a string structure that comprises a plurality of fields comprises:

for each given field of the plurality of fields, summing character lengths of all data types with higher ordinal priorities than the data type that the given field represents; and for each given field of the plurality of fields, determining as a starting character position within the string structure for the given field a character position equal to the summed character lengths plus one.

* * * * *